(12) United States Patent
Nakazato

(10) Patent No.: US 9,297,783 B2
(45) Date of Patent: Mar. 29, 2016

(54) REAGENT APPLYING DEVICE AND REAGENT APPLYING METHOD FOR ELECTROPHORESIS ANALYSIS

(71) Applicant: Tokiya Nakazato, Saitama (JP)

(72) Inventor: Tokiya Nakazato, Saitama (JP)

( * ) Notice: Subject to any disclaimer, the term of this patent is extended or adjusted under 35 U.S.C. 154(b) by 258 days.

(21) Appl. No.: 14/046,003

(22) Filed: Oct. 4, 2013

(65) Prior Publication Data

US 2014/0097085 A1    Apr. 10, 2014

(30) Foreign Application Priority Data

Oct. 9, 2012    (JP) ................................ 2012-224524

(51) Int. Cl.
*G01N 27/453* (2006.01)
*G01N 27/447* (2006.01)
*G01N 1/00* (2006.01)

(52) U.S. Cl.
CPC .... *G01N 27/44743* (2013.01); *G01N 2001/002* (2013.01)

(58) Field of Classification Search
CPC ................... G01N 2001/002; G01N 27/44743
See application file for complete search history.

(56) References Cited

U.S. PATENT DOCUMENTS 6,165,541 A * 12/2000 Merchant et al. ............ 427/2.11

FOREIGN PATENT DOCUMENTS

| JP | 05-249079 | 9/1993 |
| JP | 2000-329741 | 11/2000 |
| JP | 2004-037445 | 2/2004 |

OTHER PUBLICATIONS

CMHC (Canadian Mortgage Housing Corporation) Research Highlights Technical Series publication 97-107, which is entitled "Water Flow by Means of Capillary Action", 1997, downloaded from http://www.cmhc-schl.gc.ca/publications/en/rh-pr/tech/techdblist.cfm on Aug. 7, 2015.*

* cited by examiner

*Primary Examiner* — Alexander Noguerola
(74) *Attorney, Agent, or Firm* — Jerold I. Schneider; Schneider Rothman Intellectual Property Law Group, PLLC

(57) ABSTRACT

To provide a reagent applying device and a reagent applying method for electrophoresis analysis which make it possible to apply a reagent with a simple configuration at low cost. A reagent supplying device for supplying a reagent to the surface of a gel in electrophoresis analysis includes a reagent applying tool which is a plate-shaped body. The reagent applying tool includes at least one reagent holding section which penetrates the reagent applying tool in a thickness direction and which holds a reagent by capillary action, and a reagent spreading section for spreading, on the surface of the gel, a reagent supplied from a lower-side opening of the reagent holding section when the reagent applying tool is placed on the gel.

6 Claims, 11 Drawing Sheets

FIG.9A   FIG.9B

REAGENT APPLYING DEVICE AND REAGENT APPLYING METHOD FOR ELECTROPHORESIS ANALYSIS

CROSS-REFERENCES TO RELATED APPLICATIONS

This application claims the benefit of Japanese Patent Application No. 2012-224524, filed Oct. 9, 2012, which is hereby incorporated by reference herein in its entirety.

BACKGROUND OF THE INVENTION

1. Field of the Invention

The present invention relates to a reagent applying device and a reagent applying method for electrophoresis analysis, and particularly relates to a reagent applying device and a reagent applying method for electrophoresis analysis, wherein in biochemical examination and study, analysis samples are spread on a gel which is a support and are reacted with a reagent to measure a resultant substance.

2. Description of the Related Art

A conventional reagent applying device is placed on the surface of a gel and thereafter, a reagent is injected onto each sample through the reagent applying device by using a pipette (see, for example, Japanese Patent Laid-open No. 2000-329741).

In order to supply the reagent to the surface of the gel in the above reagent injecting process, a mask is used. For example, the following mask is known (see, for example, Japanese Patent Laid-open No. H05-249079 (1993)): a mask for depositing and spreading one or more types of liquids along one or more predetermined zones on the surface of the gel, the mask being used to receive a plurality of liquids for covering various incubation surfaces.

The conventional reagent applying device in which a reagent is injected onto each sample through a mask cannot achieve a result without manual work for measurement of a resultant substance. This work is directly conducted on a gel with precision, and requires proficiency and takes time.

As a technique for eliminating the troublesome work, there is a device for automating the operation of injecting a reagent by using a pipette. However, this technique has a problem that the device is complicated, large, and expensive.

SUMMARY OF THE INVENTION

The present invention is made in view of this problem, and an object of the present invention is to provide a reagent applying device and a reagent applying method for electrophoresis analysis which make it possible to apply a reagent with a simple configuration at low cost.

In order to solve the above problem, the present invention is configured to hold a reagent in a reagent holding section of a reagent applying tool by capillary action.

When this reagent applying tool is placed on a gel, a void is formed between a reagent spreading section formed on a lower surface of the reagent applying tool and the surface of the gel. When the reagent held by the reagent applying tool contacts the surface of the gel, the reagent held by the reagent holding section of the reagent applying tool moves in the void using force generated by capillary action to spread uniformly on the gel. This spread of the reagent is achieved because the force on the supplied reagent generated by capillary action is stronger than surface tension in the reagent holding section.

According to the present invention, there is provided a reagent supplying device for supplying a reagent to the surface of a gel in electrophoresis analysis, the reagent supplying device including a reagent applying tool which is a plate-shaped body, the reagent applying tool including at least one reagent holding section which penetrates the reagent applying tool in a thickness direction and which holds a reagent by capillary action, and a reagent spreading section for spreading, on the surface of the gel, a reagent supplied from a lower-side opening of the reagent holding section when the reagent applying tool is placed on the gel.

In this regard, the reagent supplying device can be configured such that when the reagent applying tool is placed on the gel, a void is formed between the reagent spreading section and the surface of the gel, and the reagent supplied from the lower-side opening of the reagent holding section is passed to the reagent spreading section and is applied to the surface of the gel by capillary action.

Further, the reagent supplying device can be configured such that the reagent spreading section has an additional opening which penetrates the plate-shaped body in a thickness direction and air in a void formed between the reagent spreading section and the surface of the gel is pressed toward the additional opening by the reagent supplied from the lower-side opening of the reagent holding section.

Further, the reagent supplying device can be configured such that a surface of the reagent applying tool facing the gel has an open section connected to a void formed between the reagent spreading section and the surface of the gel, and air in the void is pressed toward the open section by the reagent supplied from the lower-side opening of the reagent holding section.

Further, the reagent holding section can be in the shape of a cylinder or an elliptical cylinder.

Further, the reagent supplying device can further include means for blowing air from above the reagent applying tool to supply the reagent held by the reagent holding section toward a lower side of the reagent holding section.

According to another aspect of the present invention, there is provided a reagent supplying method for supplying a reagent to the surface of a gel in electrophoresis analysis, including the steps of: injecting a reagent into at least one reagent holding section included in a reagent applying tool which is a plate-shaped body, the at least one reagent holding section penetrating the reagent holding section in a thickness direction and holding the reagent by capillary action; placing the reagent applying tool on the gel; and supplying the held reagent from a lower-side opening of the reagent holding section, wherein the reagent supplied from the lower-side opening of the reagent holding section is passed to a reagent spreading section formed in a lower side of the reagent holding section and is applied to the surface of the gel.

According to the present invention, it becomes possible to provide a reagent supplying device for electrophoresis analysis having a simple configuration at low cost.

Further, a plurality of types of reagents are firstly provided on the reagent applying tool, and these reagents can be simultaneously spread on the surface of the gel. Accordingly, it becomes possible to easily automate, at low cost, the manual work necessary for electrophoresis analysis.

Further, it becomes possible to firstly provide a reagent on the reagent applying tool at a location different from the location of an analysis device and the like.

Further features of the present invention will become apparent from the following description of exemplary embodiments (with reference to the attached drawings).

BRIEF DESCRIPTION OF THE DRAWINGS

FIG. 3A is a cross-sectional view of a portion including a reagent holding section of a side contact type, and FIGS. 3B and 3C are cross-sectional views of portions including reagent holding sections of a side open type;

FIG. 9A is an external perspective view of a filter paper supporting tool in accordance with the embodiment of the present invention, FIG. 9B is a side view thereof as seen from an arrow B in FIG. 9A.

DESCRIPTION OF THE EMBODIMENTS

An embodiment of the present invention will be explained in detail below with reference to the attached drawings.

Figure 1:
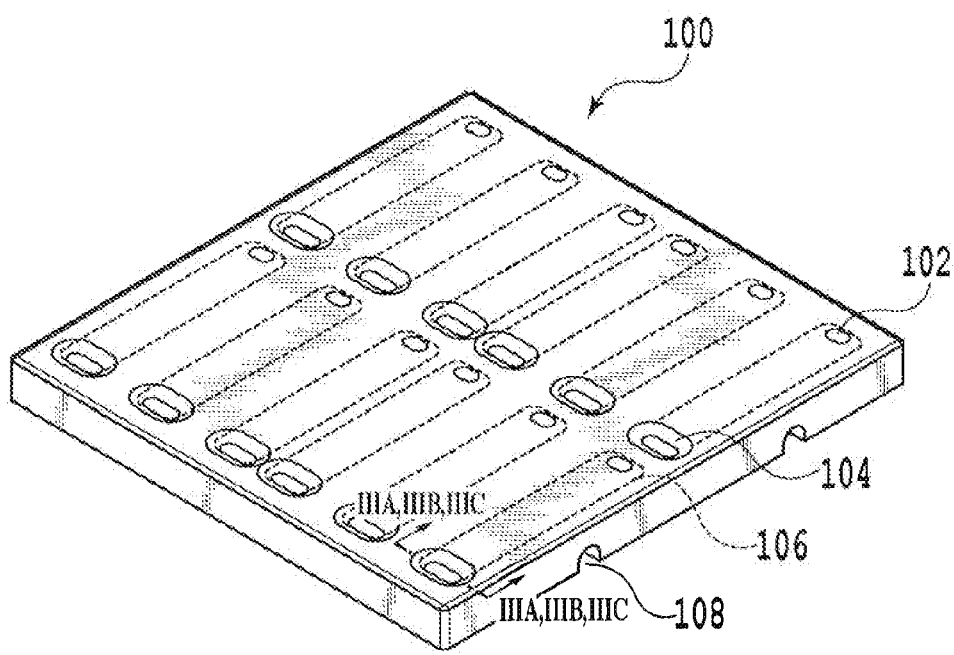
FIG. 1 is an external perspective view of a reagent applying tool included in a reagent supplying device in accordance with an embodiment of the present invention.
Figure 2:
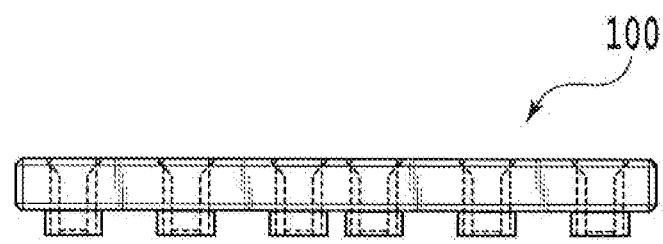
FIG. 2 is a side view of the reagent applying tool in accordance with the embodiment of the present invention as seen from a longitudinal direction of a reagent spreading section.

FIG. 1 is an external perspective view of a reagent applying tool included in a reagent supplying device in accordance with the present embodiment. FIG. 2 is a side view of the reagent applying tool.

A reagent supplying device for supplying a reagent to the surface of a gel in electrophoresis analysis includes a reagent applying tool 100 which is formed in the shape of a plate and a reagent applying tool supporting unit which will be described later. The reagent applying tool 100 has a reagent holding section 104 which penetrates the plate-shaped body in a thickness direction. The reagent holding section 104 holds a reagent in an amount which is equal to or lower than a predetermined amount by capillary action. In the example shown in FIG. 1, the reagent applying tool 100 has twelve reagent holding sections 104.

An opening of the reagent holding section 104 can be in the shape of a cylinder or an elliptical cylinder.

Further, the reagent applying tool 100 has a reagent spreading section 106 (lane) on a lower-side surface (in other words, a surface facing a gel in a case where the reagent applying tool 100 is placed on the gel). The reagent spreading section 106 is formed in the shape of a long rectangle. In the embodiment shown in FIG. 1, the reagent applying tool 100 has a total of twelve (six columns×two rows) reagent spreading sections 106. However, the present invention is not limited to this.

Further, the reagent applying tool 100 has a notch 108 for engaging a pin provided to the reagent applying tool supporting unit which will be described later when the reagent applying tool supporting unit holds the reagent applying tool.

Figure 3A:
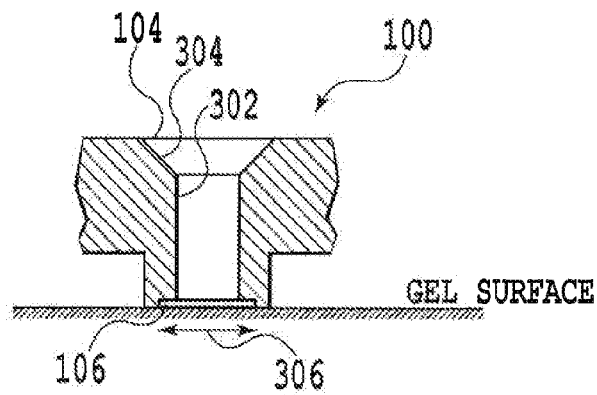
FIGS. 3A to 3C show examples of cross-sectional views of the reagent applying tools in accordance with the embodiment of the present invention.
Figure 3B:
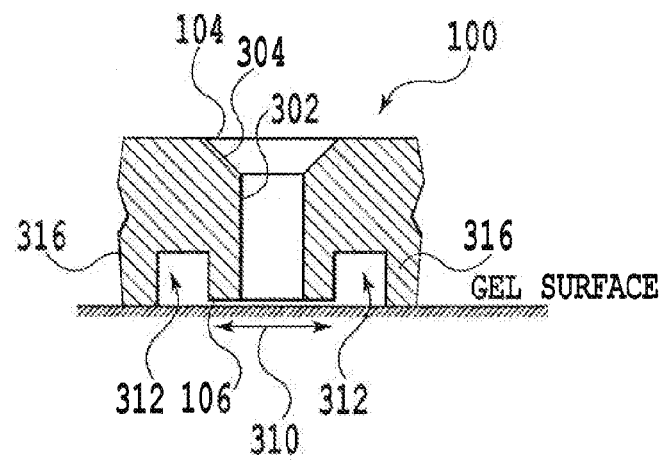
Figure 3C:
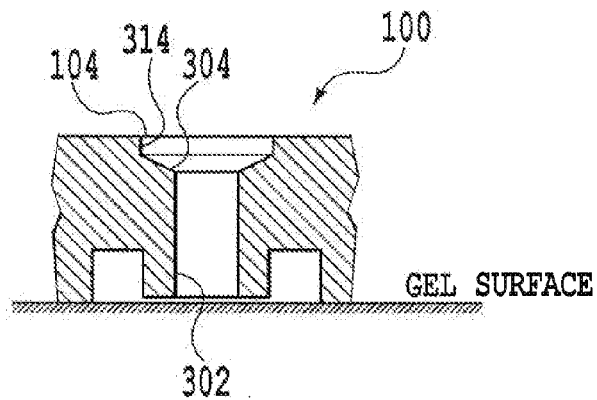

FIGS. 3A to 3C show examples of cross-sectional views of the reagent applying tools 100 as taken along a line shown by arrows IIIA and IIIA, IIIB and IIIB, and IIIC and IIIC in FIG. 1. FIG. 3A is a cross-sectional view of a reagent holding section of the reagent applying tool 100 of a side contact type and FIGS. 3B and 3C are cross-sectional views of reagent holding sections of the reagent applying tools 100 of a side open type. In FIGS. 3A and 3B, the reagent holding section 104 is composed of a funnel-shaped storing section 304 and a cylindrical capillary section 302. A reagent is held in the capillary section 302 by capillary action. The storing section 304 holds an additional reagent without capillary action and also has the function of facilitating injection of a reagent with a pipette.

Incidentally, as in the example shown in FIG. 3C, an additional cylindrical storing section 314 can be further formed in an upper portion of the reagent applying tool 100. Further, the capillary section 302 only has to have a shape such that the capillary section 302 can hold a reagent by capillary action. For example, the capillary section 302 can be inclined.

The reagent spreading section 106 is provided on a surface facing the surface of a gel. When the reagent applying tool 100 is placed on the gel, a void having a width shown by an arrow 306, 310 is formed between the reagent spreading section and the surface of the gel. In a case where the reagent applying tool is of a side contact type, a side portion of the reagent spreading section 106 is in close contact with the surface of the gel as shown in FIG. 3A. On the other hand, in a case where the reagent applying tool is of a side open type, a supporting column 316 is in close contact with the surface of the gel as shown in FIGS. 3B and 3C. The void having the width shown by the arrow 310 communicates with an open section 312 formed by the supporting column 316. Incidentally, in the examples shown in FIGS. 3B and 3C, the supporting column 316 is provided along the longitudinal direction of the reagent spreading section 106, but the supporting column can be formed anywhere as long as the open section 312 can be formed.

The reagent holding section 104 can hold a reagent in an amount which is equal to or lower than a predetermined amount. The holding capacity of the reagent holding section 104 can be measured by using a reagent, but there is a case where measurement is difficult as in the case of using a viscous reagent. Accordingly, it is desirable to measure a standard holding capacity by using purified water and use the standard holding capacity. The maximum holding capacity of the reagent holding section 104 is preferably set at an amount such that the reagent holding section 104 is filled with purified water and a liquid surface in a lower outlet is flat or concave with a center portion thereof being raised a little. Further, it is preferable to set the maximum holding capacity at an amount such that the center of the liquid surface of an upper injection opening of the reagent holding section 104 is at the lowest level. Further, the reagent holding capacity can be set to include the holding capacity of the storing section 304 as well.

Incidentally, the reagent holding section 104 can be filled with purified water in a state in which a liquid surface in the lower outlet is convex or in a state in which a liquid surface in the upper injection opening is flat or convex. However, this is inappropriate because surface tension on the upper liquid surface acts and a reagent drops because of slight vibration.

Further, the opening of the reagent holding section 104 can be in the shape of an elliptical cylinder having a major axis in a lateral direction in the drawing in a case where the reagent holding section 104 is of a side contact type. However, in a case where the reagent holding section 104 is of a side open type, the reagent holding section 104 is preferably cylindrical so that at the time of injecting a reagent, the amount of the reagent spread to the side can be reduced. Further, in a case where a reagent contains a surfactant and the reagent holding section 104 of a side open type is used, the reagent is likely to flow from a void, and it is necessary to minimize vibration during use.

The reagent applying tool 100 including each reagent holding section 104 holding a reagent is placed on a gel. A reagent held by the reagent holding section 104 flows from the lower-side opening when the reagent applying tool 100 is vibrated. The flowing reagent spreads in the void by capillary action, whereby the reagent is applied to the surface of the gel. The spread reagent is applied to an area which has a width shown by an arrow 306, 310 and which extends in a longitudinal direction (that is, a direction orthogonal to a plane of FIGS. 3A to 3C).

Figure 4A:
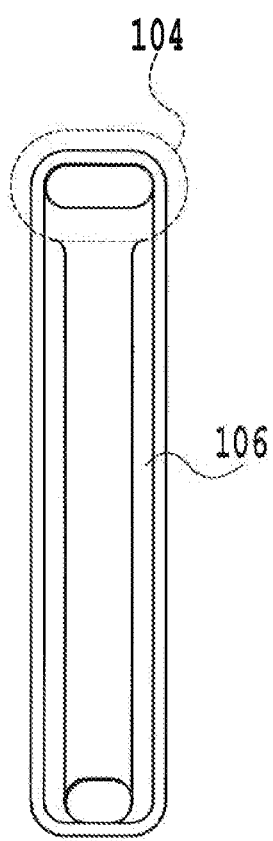
FIG. 4A is a view of a portion of a reagent applying tool of a side contact type including a reagent spreading section as seen from below.
Figure 4B:
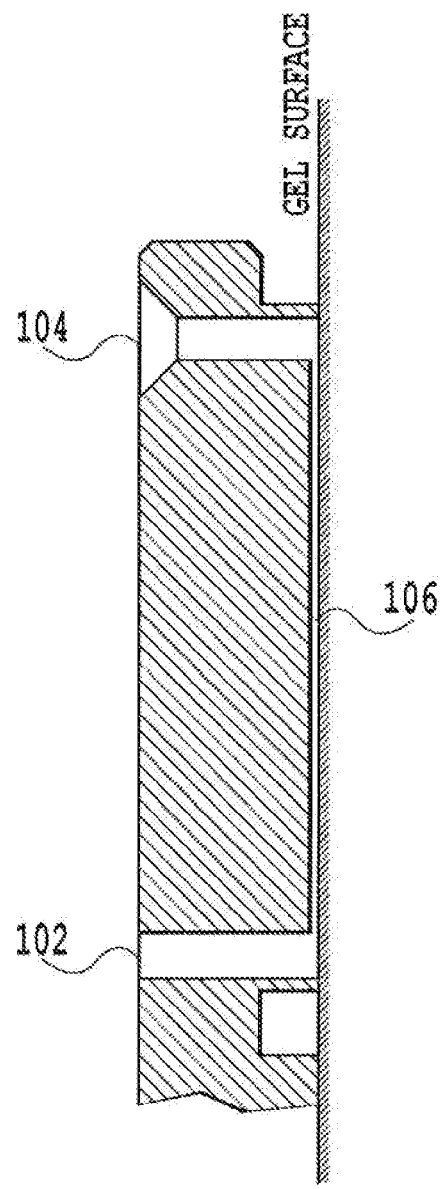
FIG. 4B is a side cross-sectional view of a reagent spreading section which is in contact with the surface of a gel.

FIG. 4A is a view of a portion of the reagent applying tool 100 of a side contact type including the reagent spreading section 106 as seen from below, and FIG. 4B is a side cross-sectional view of the reagent spreading section 106 which is in contact with the surface of a gel.

In the reagent applying tool 100 of a side contact type shown in FIG. 4A, at one end of the reagent spreading section 106 formed in the shape of a long rectangle, the reagent holding section 104 is formed to penetrate the reagent applying tool 100 in a thickness direction. Further, at the other end of the reagent spreading section 106, an air vent 102 is formed to penetrate the reagent applying tool 100 in a thickness direction. When the reagent flowing from the opening of the lower side of the reagent holding section 104 spreads in a void between the reagent spreading section 106 and the surface of the gel by capillary action, air in the void is pressed toward the air vent 102 by the reagent.

On the other hand, in a case where the reagent applying tool 100 is of a side open type as shown in FIGS. 3B and 3C, instead of the air vent, the reagent applying tool 100 has an open section 312 along a longitudinal direction of the reagent spreading section 106 on the lower surface of the reagent applying tool 100. When the reagent flowing from the opening of the lower side of the reagent holding section 104 spreads in a void between the reagent spreading section 106 and the surface of the gel by capillary action, air in the void is pressed toward the open section 312 by the reagent supplied from the lower side of the opening. Incidentally, there is a case where a reagent flows beyond the area having the width shown by the arrow 310, but the supporting column 316 prevents the reagent from being spread outside the reagent spreading section 106.

Preferably, the void in the reagent spreading section 106 is directly connected to the lower-side opening of the reagent holding section 104.

Figure 5:
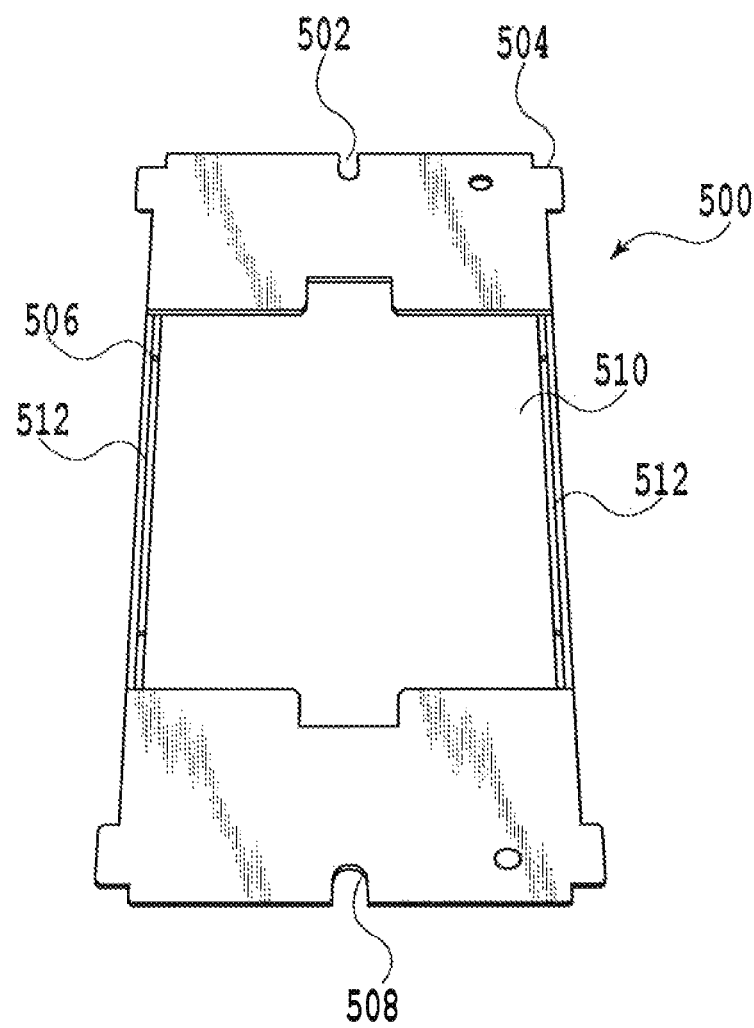
FIG. 5 is an external perspective view of a reagent applying tool supporting unit in accordance with the embodiment of the present invention.

FIG. 5 is an external perspective view of a reagent applying tool supporting unit in accordance with the present embodiment. The reagent applying tool supporting unit 500 has, as its center, an opening 510 into which the reagent applying tool 100 is to be inserted. Further, the reagent applying tool supporting unit 500 has four pins 506 for supporting the reagent applying tool 100 on side surfaces 512 which are provided to a pair of sides constituting the opening.

Figure 7:
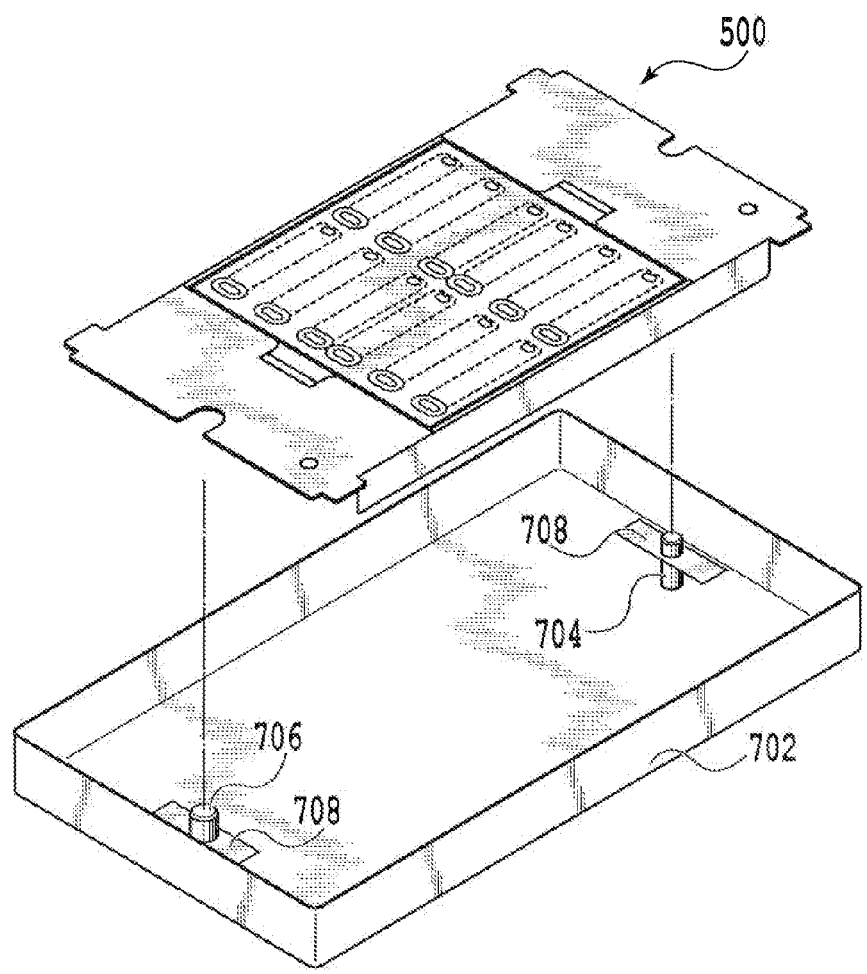
FIG. 7 is a view for explaining a mechanism for holding, in a tray, the reagent applying tool supporting unit in accordance with the embodiment of the present invention.

Further, notches 502 and 508 are formed at an upper end and a lower end of the reagent applying tool supporting unit 500, respectively ("upper" and "lower" refer to positions in the drawings). The notch 508 is larger than the notch 502. These notches are provided to engage pins 704 and 706 provided to a tray 702 as shown in FIG. 7. In the example shown in FIG. 7, the pins 704 and 706 have sizes corresponding to the notches 502 and 508, respectively. Further, a stopper 708 is provided to each of the pins 704 and 706. Accordingly, when the notches 502 and 508 engage the pins 704 and 706, the reagent applying tool supporting unit 500 is fixed at the level of the stoppers, and floats so that a reagent held by the reagent holding section 104 of the reagent applying tool 100 is not attached to the tray 702.

Further, vane-like members 504 are provided at four positions in the reagent applying tool supporting unit 500. A conveyance lift can move the reagent applying device 100 by supporting the vane-like members 504.

Figure 6:
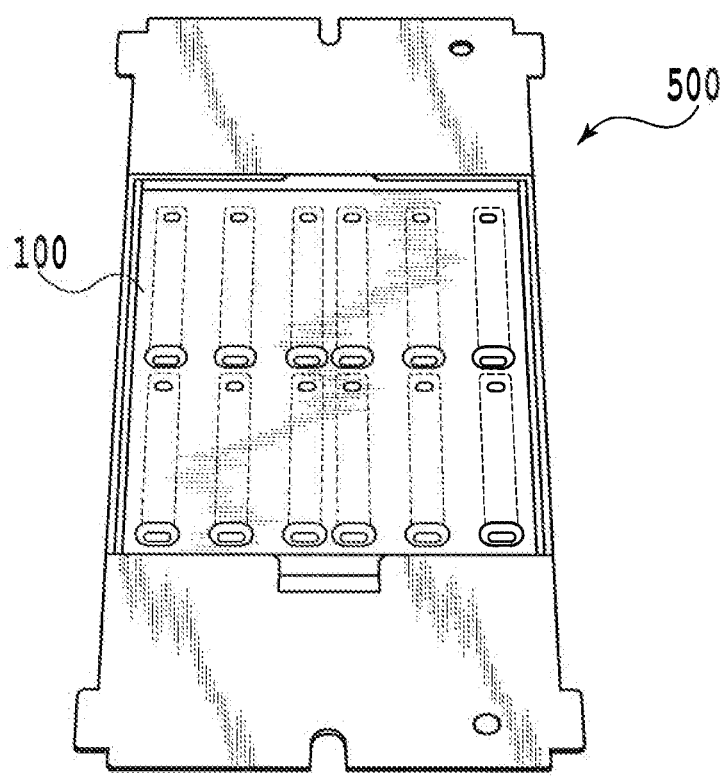
FIG. 6 is an external perspective view of the reagent applying tool supporting unit which holds the reagent applying tool in accordance with the embodiment of the present invention.

FIG. 6 is an external perspective view of the reagent applying tool supporting unit 500 holding the reagent applying tool 100. Pins 506 at four positions in the reagent applying tool supporting unit 500 fit into notches 108 in the reagent applying tool 100, thereby supporting the reagent applying tool 100. The reagent applying tool 100 can be attached to or detached from the pins 506 by vertically moving the reagent applying tool 100 relative to the reagent applying tool supporting unit 500 which is positioned horizontally. In this manner, the reagent applying tool supporting unit 500 supporting the reagent applying tool 100 is attached to the tray 702 as shown in FIG. 7 and the tray as a whole can be conveyed.

Figure 8A:
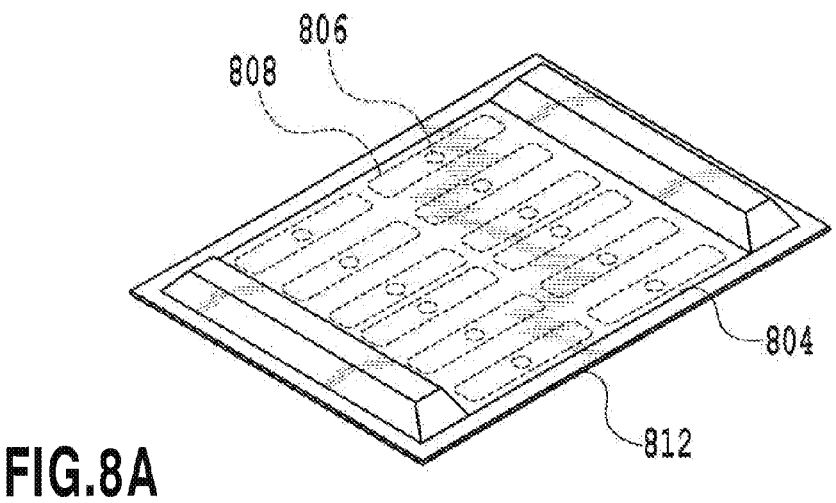
FIG. 8A is an external perspective view of a gel film used for the embodiment of the present invention.

FIG. 8A is an external perspective view of a gel film used in the present embodiment. A gel film 804 provided on a plate 812 includes supports such as agarose, agar, and polyacrylamide gel. Regarding application of an analysis sample, in order to improve absorption of a sample and a reagent by a gel, a certain amount of a buffer of a gel film is absorbed by filter paper, and then an analysis sample is extracted from a sample stage, put on an applicator, and applied to the gel film 804. The analysis sample includes serum protein, isozyme, lipoprotein, and the like. The application position of the analysis sample varies depending on an item to be examined. In the example shown in FIG. 8A, the analysis sample is applied to a center position indicated by a reference numeral 806 on the gel film 804.

The reagent is applied to a position indicated by a reference numeral 808. As the reagent, a well-known reagent is used. For example, it is possible to use, in the same manner, well-known reagents such as a lactate dehydrogenase (LDH) isozyme reagent, a creatine kinase (CK) isozyme reagent, an alkaline phosphatase isozyme reagent, an amylase isozyme reagent, a cholesterol fraction reagent, a leucine amino peptidase (LAP) isozyme reagent, a gamma-glutamine transpeptidase (yGTP) isozyme reagent, a cholinesterase isozyme reagent, and an enolase isozyme reagent.

Figure 8B:
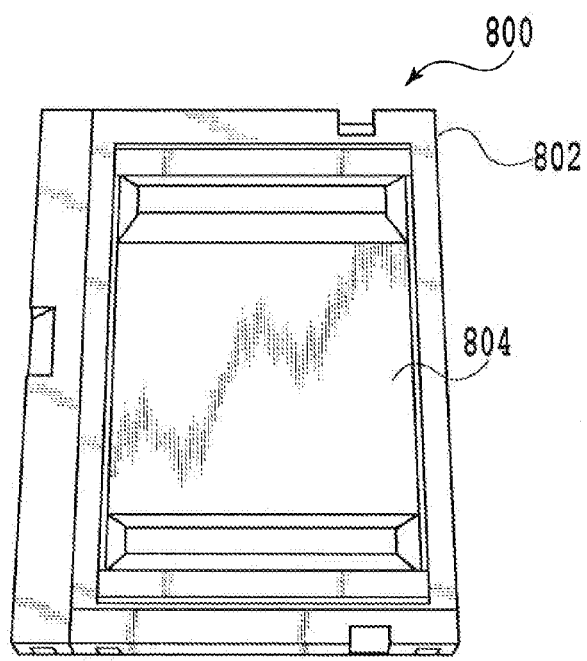
FIG. 8B is an external perspective view of a film holder holding a gel film.

This gel film 804 is held by a film holder 802 as shown in FIG. 8B.

The reagent applying tool supporting unit 500 supporting the reagent applying tool 100 is placed on the film holder 802 supporting the gel film 804 during use. When the reagent applying tool supporting unit 500 is placed on the film holder 802, the reagent applying tool 100 is placed on the gel film 804. On this occasion, the reagent applying tool 100 is detached from the reagent applying tool supporting unit 500. The reagent applying tool 100 placed on the gel film 804 floats slightly above the reagent applying tool supporting unit 500 placed on the film holder 802.

Figure 9C:
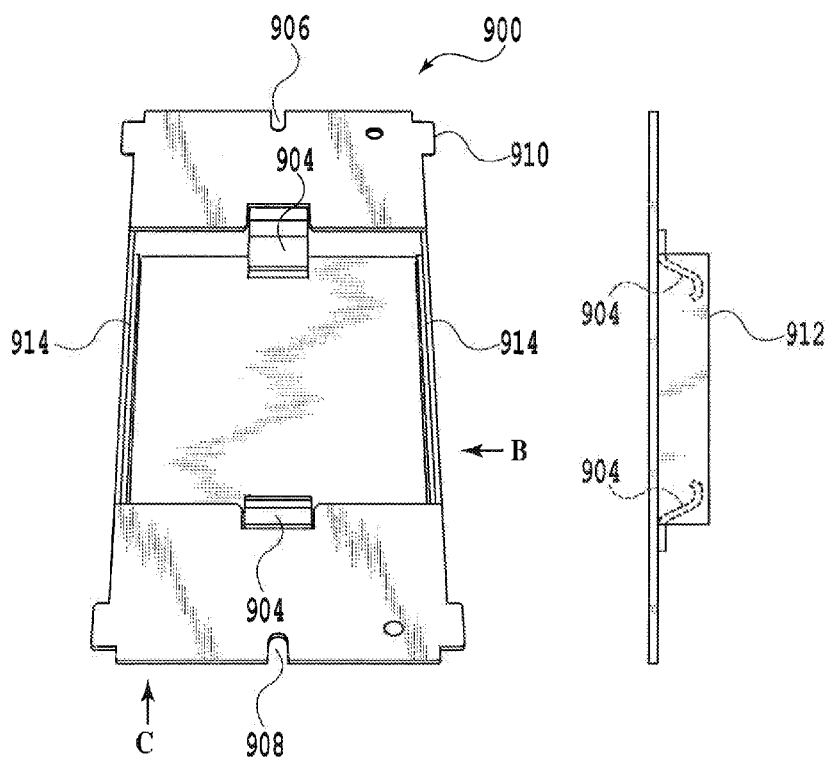
FIG. 9C is a side view thereof as seen from an arrow C in FIG. 9A.
Figure 9C:
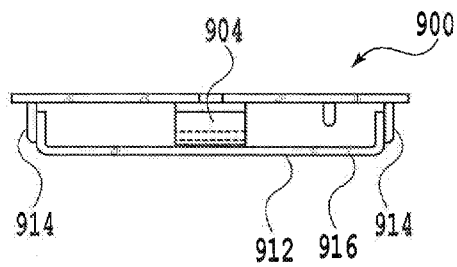

FIGS. 9A to 9C show a filter paper supporting tool for supporting filter paper for absorbing an excess reagent applied to a gel. FIG. 9A is an external perspective view of the filter paper supporting tool, FIG. 9B is a side view thereof as seen from an arrow B in FIG. 9A, and FIG. 9C is a side view thereof as seen from an arrow C in FIG. 9A. In FIG. 9A, an opening is provided at the center of the filter paper supporting tool 900. A pair of side walls 914 is fixed to sides extending in a longitudinal direction of this opening ("longitudinal direction" refers to a direction in the drawing). As shown in FIG. 9B, a staple-shaped member 916 having a filter paper mounting surface 912 is fixed to the side walls 914. Clips 904 for holding filter paper are provided to an upper portion and a lower portion of the opening as shown in FIG. 9A ("upper" and "lower" refer to positions in the drawing).

Figures 10A, 10B:
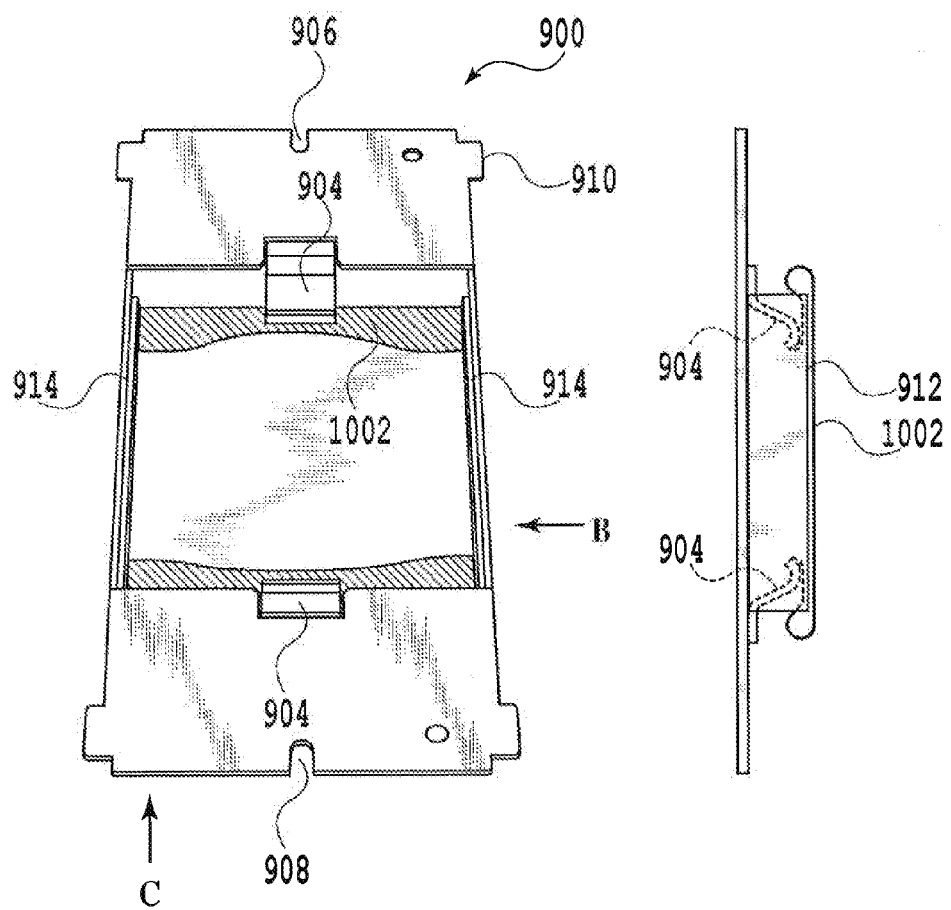
FIG. 10A is an external perspective view of a filter paper supporting tool which supports filter paper.
FIG. 10B is a side view thereof as seen from an arrow B in FIG. 10A.
Figure 10C:
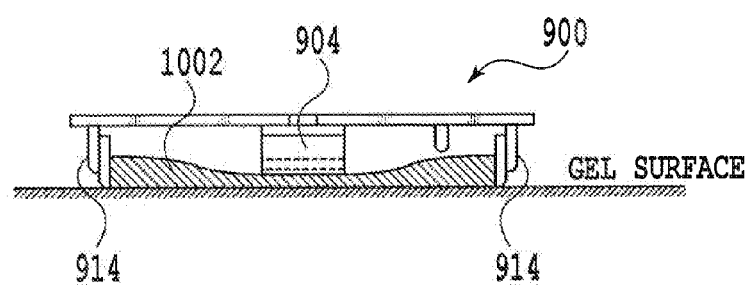
FIG. 10C is a side view thereof as seen from an arrow C in FIG. 10A.

FIGS. 10A to 10C show the filter paper supporting tool which supports filter paper. FIG. 10A is an external perspective view of the filter paper supporting tool, FIG. 10B is a side view thereof as seen from an arrow B in FIG. 10A, and FIG. 10C is a side view thereof as seen from an arrow C in FIG. 10A. Filter paper 1002 is attached to a filter paper mounting surface 912. End portions of the filter paper attached to the filter paper mounting surface 912 are folded to wrap the filter paper mounting surface 912 as shown in FIG. 10B, and are held by the clips 904. In FIG. 10C, the filter paper under the filter paper mounting surface 912 is in close contact with the surface of a gel, and can absorb an excess reagent applied to the gel.

Further, notches 906 and 908 are provided to an upper end and a lower end of the filter paper supporting tool 900 shown in FIG. 10A, respectively ("upper" and "lower" refer to positions in the drawing). The notch 908 is larger than the notch 906. These notches engage the pins 704 and 706 provided to the tray 702 shown in FIG. 7. In the example shown in FIG. 7, the pins 704 and 706 have sizes corresponding to the notches 906 and 908, respectively. Accordingly, the filter paper supporting tool 900 is attached to the tray 702 and like the reagent applying device 100, the filter paper supporting tool 900 can be carried in the tray.

Further, vane-like members 910 are provided at four positions in the filter paper supporting tool 900. A conveyance lift can move the filter paper supporting tool 900 by supporting the vane-like members 910.

Next, the specific operations of the above reagent supplying device for supplying a reagent to the surface of the gel will be explained. In the following, immunofixation will be explained as an example.

Firstly, as shown in FIG. 6, the reagent applying tool 100 is provided to the reagent applying tool supporting unit 500.

Next, a reagent is injected into the reagent holding section 104. The reagent is injected little by little after quietly applying a tip end of a pipette to an inner wall of the storing section 304 shown in FIG. 3A.

Further, the gel film 804 is subjected to electrophoresis. The film holder 802 having the gel film 804 subjected to electrophoresis is in close contact with a flat surface. In a case where a buffer is formed on the upper surface of the gel film 804 by electro-osmosis, the buffer affects absorption of a reagent by the gel film 804 and adjustment can be made by drying the buffer with a blower.

Next, when the reagent applying tool supporting unit 500 supporting the reagent applying tool 100 is caused to free-fall on the gel film 804 from a somewhat high position (for example, two or three millimeters high from the surface of the gel) such that the gel is not damaged, the reagent applying tool 100 drops under its own weight. On this occasion, the reagent applying tool 100 is placed on the gel film 804 and the reagent applying tool 100 is displaced from the reagent applying tool supporting unit 500 placed on the film holder 802 and floats slightly. Because of vibration caused by the drop of the reagent applying tool 100, a reagent flows from the reagent holding section 104 and as described above, the reagent is applied to the gel film precisely.

When the gel is weak, it is necessary to gently place the reagent applying tool 100. In this case, there appears a lane where the reagent does not contact the surface of the gel, and the reagent is not applied. In this case, the reagent can be forcefully flowed to the reagent spreading section 106 without damaging the gel by blowing air from above the reagent applying tool 100 with a blower.

When a reaction ends, the reagent applying tool 100 is removed, and the filter paper supporting tool 900 is placed on the gel film 804 to absorb an excess reagent.

The gel film 804 from which the excess reagent is absorbed is immersed in normal saline together with the film holder 802, and protein and the reagent which are not fixed to the gel by an antigen-antibody reaction are washed away, thereby performing deproteinization.

Next, after normal saline is absorbed from the surface of the gel film 804 which is subjected to deproteinization by using filter paper again, the gel film 804 is dyed with a stain solution. A dye reagent is spread over the gel film 804. Further, a stain solution which is not involved in dying of the gel is washed away. In this washing process, a solution containing about 3% acetic acid or 0.3% citric acid, for example, is generally used.

Thereafter, the decolored gel is dried and the dried gel film 804 is read by a scanner to perform image processing for the gel film.

The preferred embodiment of the present invention has been explained so far. However, it is needless to say that the present invention is not limited to the above embodiment, and that other various embodiments can be carried out as well.

For example, in the above embodiment, the reagent applying tool and the reagent applying tool supporting unit are separate. However, they can be integrally formed. In this case, it is desirable to reduce their weight so as not to damage agarose when spreading a reagent.

Figure 11:
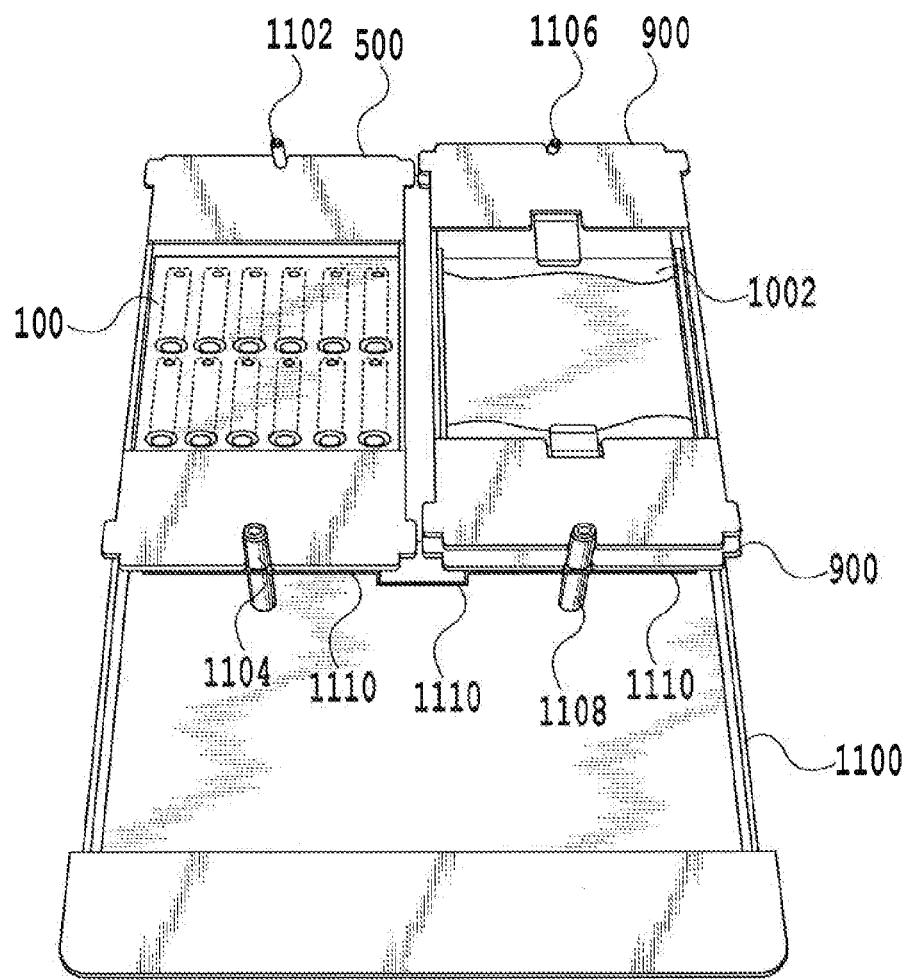
FIG. 11 is an external perspective view of a tray to which the reagent applying tool supporting unit and the filter paper supporting tool are attached in accordance with the embodiment of the present invention.

Further, as shown in FIG. 11, the reagent applying tool supporting unit and the filter paper supporting tool can be simultaneously conveyed by using one tray. In the example shown in FIG. 11, the one reagent applying tool supporting unit 500 is attached by pins 1102, 1104 provided to a tray 1100, and the two filter paper supporting tools 900 are attached by pins 1106, 1108. Further, stoppers 1110 are provided to the pins 1102, 1104, 1106, and 1108.

Further, the number of the reagent spreading sections constituting the reagent applying tool is not limited to the number in the above embodiment. For example, the total number of the reagent spreading sections can be nine (three columns× three rows).

Further, when the size of the reagent applying unit is large, there is a case where the reagent applying unit contacts a gel at a certain angle and an environment for contact with the gel changes. Accordingly, when portions of the reagent spreading section can operate independently, the reagent spreading section can be stably placed on the gel. For example, in the above embodiment, six columns×two rows of the reagent spreading sections constitute the reagent applying tool. However, the reagent spreading sections can be configured such that each row or each one of the reagent spreading sections can be independently attached to or detached from the reagent applying tool supporting unit.

This embodiment is also within the scope of the claims as long as the embodiment does not go beyond the scope of the present invention.

The present invention can be used to spread one or more types of reagents for electrophoresis analysis using a gel and particularly can be used to apply an antiserum for immunofixation.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A reagent supplying device for supplying a reagent to a surface of a gel for use in electrophoresis analysis, the reagent supplying device comprising:
    a reagent applying tool which is a plate-shaped body, the reagent applying tool including:
    at least one reagent holding section which penetrates the reagent applying tool in a thickness direction and which holds a reagent by capillary action; and
    a reagent spreading section for spreading, on the surface of the gel, a reagent supplied from a lower-side opening of the reagent holding section when the reagent applying tool is placed on the gel,
    wherein a surface of the reagent applying tool facing the gel has an open section connected to a void formed between the reagent spreading section and the surface of the gel, and air in the void is pressed toward the open section by the reagent supplied from the lower-side opening of the reagent holding section.

2. The reagent supplying device as claimed in claim 1, wherein when the reagent applying tool is placed on the gel, a void is formed between the reagent spreading section and the surface of the gel, and the reagent supplied from the lower-side opening of the reagent holding section is passed to the reagent spreading section and is applied to the surface of the gel by capillary action.

3. The reagent supplying device as claimed in claim 1, wherein the reagent spreading section has an additional opening which penetrates the plate-shaped body in a thickness direction and air in a void formed between the reagent spreading section and the surface of the gel is pressed toward the additional opening by the reagent supplied from the lower-side opening of the reagent holding section.

4. The reagent supplying device as claimed in claim 1, wherein the reagent holding section is in the shape of a cylinder or an elliptical cylinder.

5. The reagent supplying device as claimed in claim 1, further comprising a blower for blowing air from above the reagent applying tool to supply the reagent held by the reagent holding section toward a lower side of the reagent holding section.

6. A reagent supplying method for supplying a reagent to a surface of a gel for use in electrophoresis analysis, comprising the steps of:
    injecting a reagent into at least one reagent holding section included in a reagent applying tool which is a plate-shaped body, the at least one reagent holding section penetrating the reagent holding section in a thickness direction and holding the reagent by capillary action;
    placing the reagent applying tool on the gel; and
    supplying the held reagent from a lower-side opening of the reagent holding section,
    wherein the reagent supplied from the lower-side opening of the reagent holding section is passed to a reagent spreading section formed in a lower side of the reagent holding section and is applied to the surface of the gel.

* * * * *